(12) United States Patent
Zhou et al.

(10) Patent No.: US 6,722,403 B2
(45) Date of Patent: Apr. 20, 2004

(54) AUTOMATED APPARATUS FOR DISPENSING MEASURED QUANTITIES OF POWDER TO CONTAINERS IN AN ARRAY

(75) Inventors: Peng Zhou, Newtown, PA (US); Edward Joseph Kuspiel, Rahway, NJ (US); Waldemar Ruediger, New Hope, PA (US); Alexander Bertok, Edison, NJ (US); Carl J. Trpisovsky, Kendall Park, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 50 days.

(21) Appl. No.: 10/057,370

(22) Filed: Jan. 24, 2002

(65) Prior Publication Data

US 2003/0136463 A1 Jul. 24, 2003

(51) Int. Cl.[7] ................................................ F62B 11/00
(52) U.S. Cl. .................... 141/129; 141/83; 141/153; 141/178; 141/181; 141/233; 222/52; 222/77; 222/413
(58) Field of Search .............................. 222/52, 55, 56, 222/63, 77, 150, 271, 330, 333, 336, 342, 411, 412, 413; 141/83, 94, 139, 129, 153, 178, 181, 186, 231, 232, 233, 234, 237, 242, 243

(56) References Cited

U.S. PATENT DOCUMENTS

| | | | |
|---|---|---|---|
| 3,806,002 A | * | 4/1974 | Mills et al. ................. 222/626 |
| 4,804,111 A | | 2/1989 | Ricciardi et al. |
| 4,844,296 A | | 7/1989 | Hayashi et al. |
| 5,421,513 A | | 6/1995 | Gubler |

* cited by examiner

Primary Examiner—Gregory L. Huson
Assistant Examiner—Peter deVore
(74) Attorney, Agent, or Firm—Deanna L. Baxam

(57) ABSTRACT

A bifurcated bracket carries two powder dispensing assemblies. Each assembly includes a powder reservoir and a rotatable screw received within a compliant silicone sleeve. The outer diameter of the screw is slightly larger than the inner diameter of the sleeve such that the screw blade maintains direct contact with the sleeve wall as the screw is rotated. The bracket is sequentially moved to align each assembly with containers in two arrays. Each array of containers is situated in a tray. The trays are manually positioned on independent scales which generate signals that are a function of the sensed weight of each array. To fill each container, the screw in the aligned assembly is rotated at a high rate for an initial period and then at a slower rate. The scales are operational only during the slower rate period. Assembly movement and screw rotation are computer controlled.

61 Claims, 8 Drawing Sheets

AUTOMATED APPARATUS FOR DISPENSING MEASURED QUANTITIES OF POWDER TO CONTAINERS IN AN ARRAY

The present invention relates to powder dispensing mechanisms and more particularly to an automated apparatus for accurately and rapidly dispensing measured quantities of powder to containers in one or more arrays.

Although the present invention has been developed for use in pharmaceutical laboratories to automatically perform accurate and rapid weighing of milligram quantities of resin powder into trays carrying arrays of NanoKans, this apparatus is suitable for many other applications in which precise quantities of powder must be dispensed quickly and efficiently. Thus, while the invention will be described in the context of the pharmaceutical application for purposes of illustration, the invention should not be construed as being limited to that particular environment.

Many pharmaceutical applications require the introduction of relatively small quantities of powders which must be accurately measured by weight. In practice, this has proven extremely difficult to accomplish, particularly if precisely measured quantities of the powder must be dispensed rapidly into large numbers of containers.

The flow characteristics of powders vary widely due to particle size, electrostatic properties, the effects of variations in humidity, the surface properties of the particles and the tendency of the particles to adhere to various surfaces. Many different types of powder dispensers have been utilized, including those employing suction and vibratory type feed mechanisms, as well as single and double screw conveyors with various pitches and configurations. However, for one reason or another, none of these known powder dispensers has proved to be sufficiently accurate and rapid for use under all conditions.

Examples of screw type dispensers are found in U.S. Pat. No. 4,844,296 issued Jul. 4, 1989 to Torahiko et al., entitled "Apparatus and Method for Quantitatively Delivering Food Materials", in U.S. Pat. No. 4,804,111 issued Feb. 14, 1989 to Ricciardi et al., entitled "Mechanism For Metering Solid Materials Which Flow in a Manner Similar to Liquids"; and in U.S. Pat. No. 5,421,513, issued Jun. 6, 1995 to Gubler, entitled "Conveying Device for Exact Metering, Wherein At Least One Projecting Body is Rotated in an Inner, Disrupted Threaded Groove, and a Use Therefor". The Gubler patent discloses an approach to the problem of surface adherence which utilizes brushes and a sleeve with inner threaded grooves.

The present invention also employs a screw-type conveyor but differs from the screw conveyors of the prior art where the screw is situated within a rigid enclosure with the edge of the screw blade spaced from the interior surface of the enclosure wall. In the present invention, a vertical screw is situated within a compliant sleeve with the screw blade in direct contact with the interior surface of the sleeve wall, resulting in a positive feed system in which the quantity of powder being dispensed can be very accurately controlled, under all conditions, even when the powder is dispensed rapidly.

This is accomplished by utilizing a section of conventional silicone tubing as the sleeve which surrounds the screw so as to form a confined helical channel within the sleeve along which the powder is moved as the screw is rotated. The inner diameter of the silicone tube is selected to be slightly smaller than the outer diameter of the screw blade such that the edge of the screw blade continuously bears against the interior tube wall causing the wall to deform slightly proximate the area of blade contact. However, the silicone tube surface is smooth and resilient enough not to interfere with the rotation of the screw.

This configuration provides a positive feed and at the same time prevents powder from flowing between the screw blade and sleeve wall, and thus out of the bottom of the tube, when the screw is not rotating, such that the quantity of powder dispensed from the bottom of the sleeve can be accurately controlled. The screw maintains a constant but gentle pressure on the powder when it is rotating, without harming the powder.

The screw dispenser is capable of rapidly depositing powder into a plurality of containers, such as NanoKans, in an array. The container array is situated in a tray which rests on a scale platform. In order to enhance the speed and accuracy of the dispensing process, the rate of screw rotation for each dispensing operation is relatively high during the initial time period, when the bulk of the powder is dispensed. After a given time interval, the rotation rate of the screw is decreased and powder is dispensed more slowly, until the required weight of powder has been dispensed. The scale need be operational only during the latter period because it is only important to monitor the weight of the dispensed powder carefully as it approaches the desired level in order to deactuate the motor which drives the screw at the precise time when the desired weight of powder has been dispensed.

Automation of the dispensing process is achieved by moving the powder dispenser assembly sequentially along positions in a X-Y plane, above the powder receiving containers, and then along the Z plane to insert the assembly into each container. The dispenser assembly is moved stepwise between the dispensing positions to align it with each container in the array by a computer controlled plotter-type mechanism. One way to accomplish this is to modify a conventional Gilson liquid handler by replacing the liquid dispensing probe with the powder dispenser assembly of the present invention. Computer control is employed to cause the powder dispenser assembly to move sequentially through the dispensing positions to align with and be inserted into each of the containers of the array, and for actuating the drive motor for the screw to dispense a measured quantity of powder to each container, in turn.

Preferably, a bifurcated bracket is employed to simultaneously position two separate powder dispenser assemblies. Each assembly fills the containers in one of two separate trays, each tray being independently weighed by separate scales. In this way, two different powders can be dispensed simultaneously or twice as many containers can be filled at a time with the same powder.

It is therefore a prime object of the present invention to provide automated apparatus for rapidly dispensing precisely measured quantities of powder to containers in an array.

It is another object of the present invention to provide a powder dispensing assembly in which a screw is rotatably received within a compliant sleeve with the screw blade in direct contact with the interior surface of the sleeve.

It is another object of the present invention to provide a powder dispensing assembly including a screw controlled to rotate within a compliant sleeve at a relatively high rate during an initial time period and at a slower rate thereafter.

It is another object of the present invention to provide computer controlled apparatus which sequentially moves a powder dispensing assembly to predetermined positions relative to containers in an array.

It is another object of the present invention to provide an automated apparatus for rapidly dispensing precisely measured quantities of the same or different powders into containers in separate container arrays.

In accordance with one aspect of the present invention, a powder dispensing assembly is provided. The assembly includes a powder reservoir with an outlet. A compliant sleeve having an inner surface is situated proximate the reservoir outlet. A rotatable screw with a blade is provided. The screw is received within the sleeve with the blade is in contact with the inner surface of the sleeve. Drive means for rotating the screw relative to the sleeve are provided.

The outer diameter of the screw blade is at least as large, and preferably slightly larger, than the inner diameter of the sleeve. This insures that direct contact is maintained between the screw blade and the sleeve.

The sleeve preferably takes the form of a section of a silicone tube.

The assembly further comprises a rigid tube. One end of the rigid tube is received within the sleeve, spaced a short distance from the end of the screw. The other end of the tube preferably extends beyond the sleeve.

The rigid tube has an outer diameter. The outer diameter of the screw blade is approximately equal to the outer diameter of the rigid tube.

The compliant sleeve has an inner diameter. The outer diameter of the rigid tube is approximately equal to the inner diameter of the compliant sleeve.

The reservoir outlet has an outer diameter. The complaint sleeve has an outer diameter. The outer diameter of the reservoir outlet is approximately equal to the outer diameter of the compliant sleeve.

The reservoir outlet has an inner diameter. The inner diameter of the reservoir outlet is larger than the outer diameter of the screw blade and the inner diameter of the compliant sleeve.

Means are provided for retaining the compliant sleeve proximate the reservoir outlet. The retaining means comprises a second compliant sleeve, preferably in the form of a section of silicone tube. The retaining means surrounds the reservoir outlet and the sleeve.

The reservoir outlet has an end. The retaining means retains the compliant sleeve adjacent the end of the reservoir outlet.

Means are provided to removably connect the drive means and the screw. The connecting means partially extends through the reservoir. The screw is affixed to the connecting means and extends through the reservoir outlet. Means are provided for mounting the screw drive means above the reservoir.

The connecting means comprises a first part moveably mounted on the motor output shaft and spring loaded to engage a second part to which the screw is connected. The first part has a recess into which the second part is received. The recess and second part are correspondingly shaped to form a drive link when engaged. The second part is disengaged from the part to permit removal of the reservoir by moving it away from the first part, against the spring.

The reservoir has a main section and an inlet section. The inlet section extends from the main section. Preferably, the inlet section extends outwardly and upwardly from the main section.

Means are provided for controlling the drive means to rotate the screw at a first rate during a first time period and at a second rate during a second time period, for each dispensing operation. The first rate is higher than the second rate.

The assembly is adapted to dispense a predetermined weight of powder into a container. Means for weighing the container and for generating signal that is a function of the weight of powder in the container are provided. The control means receives the weight signal and deactuates the screw drive means when the predetermined weight is reached. The weighing means is operational only during the second, decreased rotation rate time period.

The assembly is adapted to dispense powder into a plurality of containers in an array. Means are provided for moving the assembly into alignment with each of the containers in the array, in sequence.

The assembly moving means includes a bracket to which the assembly is mounted. Means are provided for moving the bracket to selected positions relative to the array. The positions are selected such that the assembly aligns with a different one of the containers in each of the positions. The moving means moves the bracket along positions relative to the containers in the array.

Means are provided for weighing the array. The weighing means includes a surface upon which the array is situated and means for aligning the array with the bracket moving means.

The array is preferably situated in a tray. The aligning means includes a track fixed relative to the bracket moving means and a part having a surface adapted to abut the tray. The part is movable along the track. The track and the surface are in a fixed relationship, preferably orthogonal, to each other.

Powder may be dispensed into a plurality of containers situated in first and second arrays. To accomplish this, first and second powder dispensing assemblies are provided. Means are provided for simultaneously moving the first and second powder dispensing assemblies into alignment with the containers in each of the first and second arrays, respectively.

The assemblies moving means includes a bifurcated bracket. The bracket has first and second branches to which the first and second powder dispensing assemblies are respectively mounted. Means are provided for moving the bracket to selected positions relative to the arrays. The positions are selected such that each assembly is aligned with a different one of the containers in each of the arrays, in each of the positions. The moving means preferably moves the bracket to positions in the plane.

Means are provided for weighing each array. The weighing means includes first and second platforms upon which the first and second arrays are respectively received.

Means are provided for aligning each of the arrays with the bracket moving means. Each of the arrays is situated in a tray. The aligning means includes a track, situated between the scale platforms. The track is fixed relative to the bracket moving means. A part having first and second surfaces is adapted to abut the first and second trays, respectively. The part is moveable along the track to align the arrays. The surfaces are collinear. The collinear surfaces are fixed relative to the track.

In accordance with another aspect of the invention, automated apparatus for dispensing measured amounts of powder to containers in an array is provided. The apparatus includes an array of containers and a powder dispensing assembly. The assembly includes a powder reservoir with an outlet. A compliant sleeve is situated proximate the powder reservoir outlet. A screw is at least partially received within the sleeve. The screw has a blade which is in contact with the inner surface of the sleeve. Drive means are provided for rotating the screw. The assembly is mounted on a bracket. Means are provided for moving the bracket relative to the array to selected positions in which the assembly aligns with the containers in the array. Means for weighing the array and for generating a signal in accordance with the sensed weight are provided. Means for controlling the screw drive means in accordance with the signal are also provided.

The drive means is controlled to rotate the screw at a first rate during a first time period and at a second rate during a second time period, for each powder dispensing operation. The first rate is higher than the second rate. Means are provided for actuating the weighing means at the beginning of the second time period for each dispensing operation.

Means are provided for aligning the array with the bracket moving means. The array is situated in a tray. The aligning means positions the tray relative to the bracket moving means. The aligning means includes a track mounted in fixed relation to the bracket moving means and a part with a surface adapted to abut the tray. The part is movable along the track. The surface is in a fixed relation, preferably orthogonal, with the track.

In accordance with another aspect of the present invention, automated apparatus for dispensing measured amounts of powder to containers in first and second arrays is provided. The apparatus includes first and second powder dispensing assemblies. Each of the assemblies includes a powder reservoir with an outlet. A compliant sleeve is situated proximate the reservoir outlet. A screw is at least partially rotatably received within the sleeve. The screw has a blade which is in contact with the inner surface of the sleeve. First and second drive means for rotating the screws in the powder dispensing assemblies, respectively, are provided. Each of the assemblies is mounted on a bracket. Means are provided for moving the bracket relative to the arrays to selected positions in which each of the assemblies aligns with the containers in a different one of the arrays. Means for weighing each of the arrays and for generating first and second signals in accordance with the sensed weight of the first and second arrays, respectively, are provided. Means for controlling the first and second drive means in accordance with the first and second signals, respectively, are also provided.

To these and to such other objects which may hereinafter appear, the present invention relates to automated apparatus for dispensing measured quantities of powders to containers in an array, as set forth in detail in the following specification, recited in the annexed claims and illustrated in the accompanying drawings, in which like numerals refer to like parts, and in which:

Figure 1:
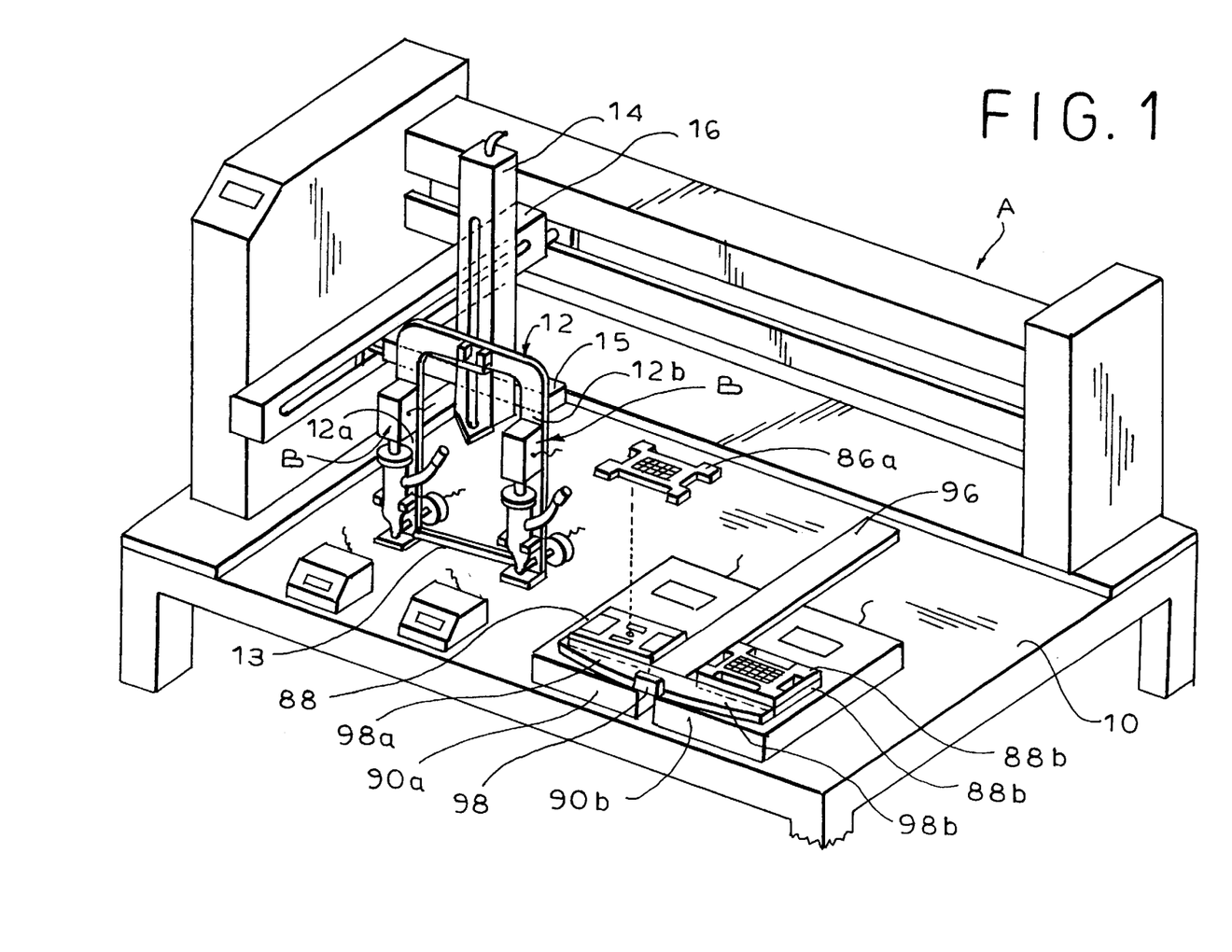
FIG. 1 is an isometric view of the automated apparatus of the present invention.
Figure 2:
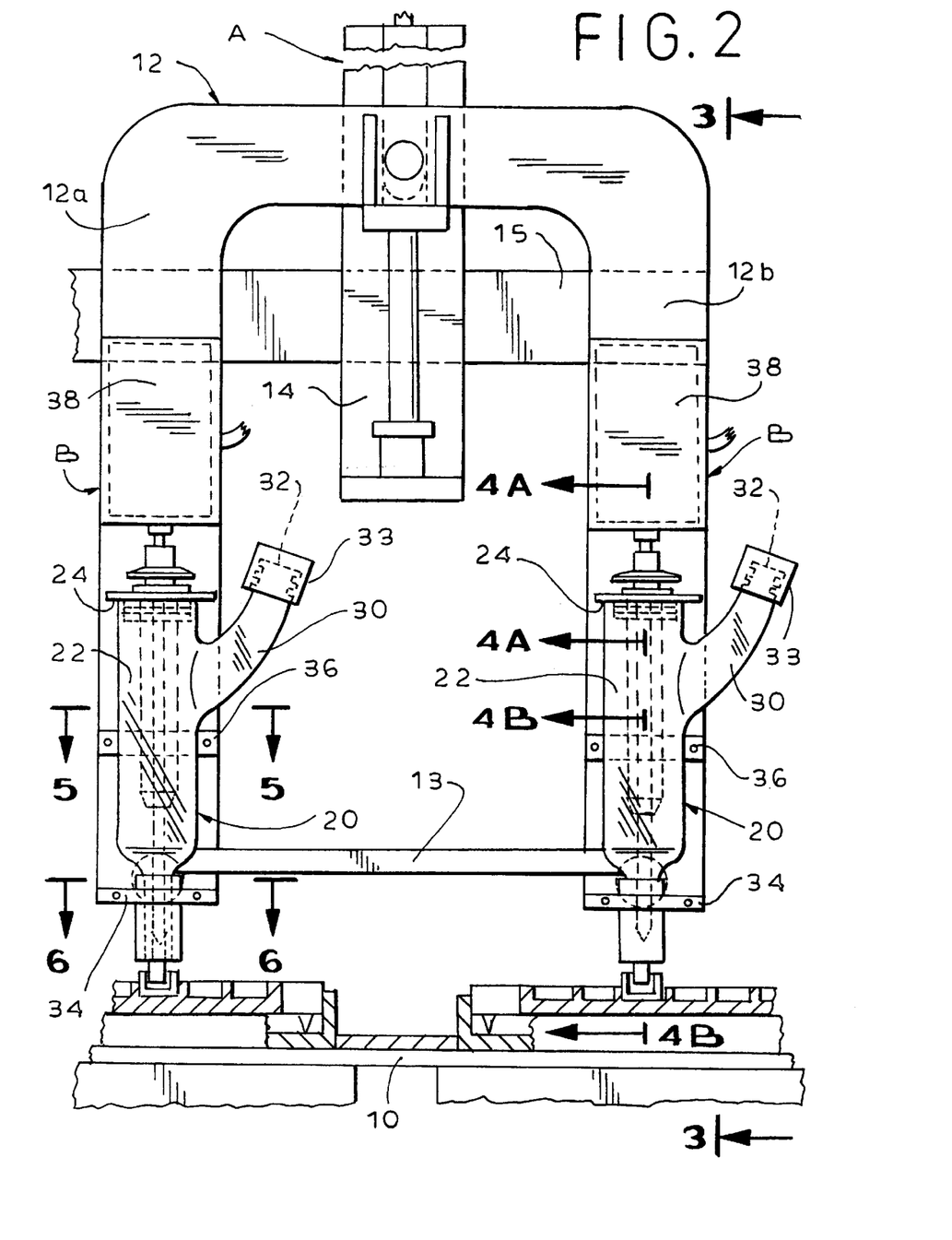
FIG. 2 is a front elevational view of the mounting bracket and powder dispensing assemblies shown in FIG. 1.

As best seen in FIGS. 1 and 2, the apparatus of the present invention includes a work surface 10, such as a table top or the like, upon which is situated a conventional plotter-type mechanism, generally designated A. Mechanism A moves a bifurcated bracket 12 stepwise through predetermined positions in the X-Y plane as well as toward and away from surface 10 along the Z axis.

Bracket 12 is mounted for movement along a vertical track 14 such that the bracket can move up and down (along the Z axis) relative to work surface 10. Vertical track 14 is carried on an arm 15 which is moveably mounted on a first horizontal track 16 extending along the side of the work surface. Arm 15 is moveable along track 16 such that bracket 12 can move (along the Y axis) relative to work surface 10. First horizontal track 16 is itself moveably mounted on a second horizontal track 18 extending along the rear of the work surface. Track 16 is moveable along track 18 such that bracket 12 can move (along the X axis) relative to work surface 10.

Bracket 12, arm 15 and track 16 are moved along track 14, track 16 and track 18 respectively by electric motors, pneumatic cylinders or any other conventional drive means. Mechanisms of this type are conventionally available and can be easily adapted for this purpose. However, a Gilson automated liquid handler, commonly found in any pharmaceutical laboratories, can be modified for use with the apparatus of the present invention by removing the liquid probe and substituting bracket 12.

Bracket 12 has two branches, 12a and 12b, as seen in FIG. 2. Each branch carries a powder dispensing assembly, generally designated B, permitting two different powders to be dispensed in two identical trays of up to 96 containers or the same powder to be dispensed into 192 containers at a time. The branches 12a, 12b are connected together at the bottom by a bar 13 for enhanced stability.

Each assembly B includes a powder reservoir 20, preferably made of transparent material such as glass or plastic, which has a main section 22 with an open mouth 24 at the top and a reduced diameter lower section 26 terminating in an open bottom 28 which functions as a powder outlet. A branch 30 extends outwardly and upwardly from main section 22. Branch 30 has an open mouth 32 which functions as a powder inlet. A screw cap 33 is provided on branch 30 to close the inlet.

Figure 3:
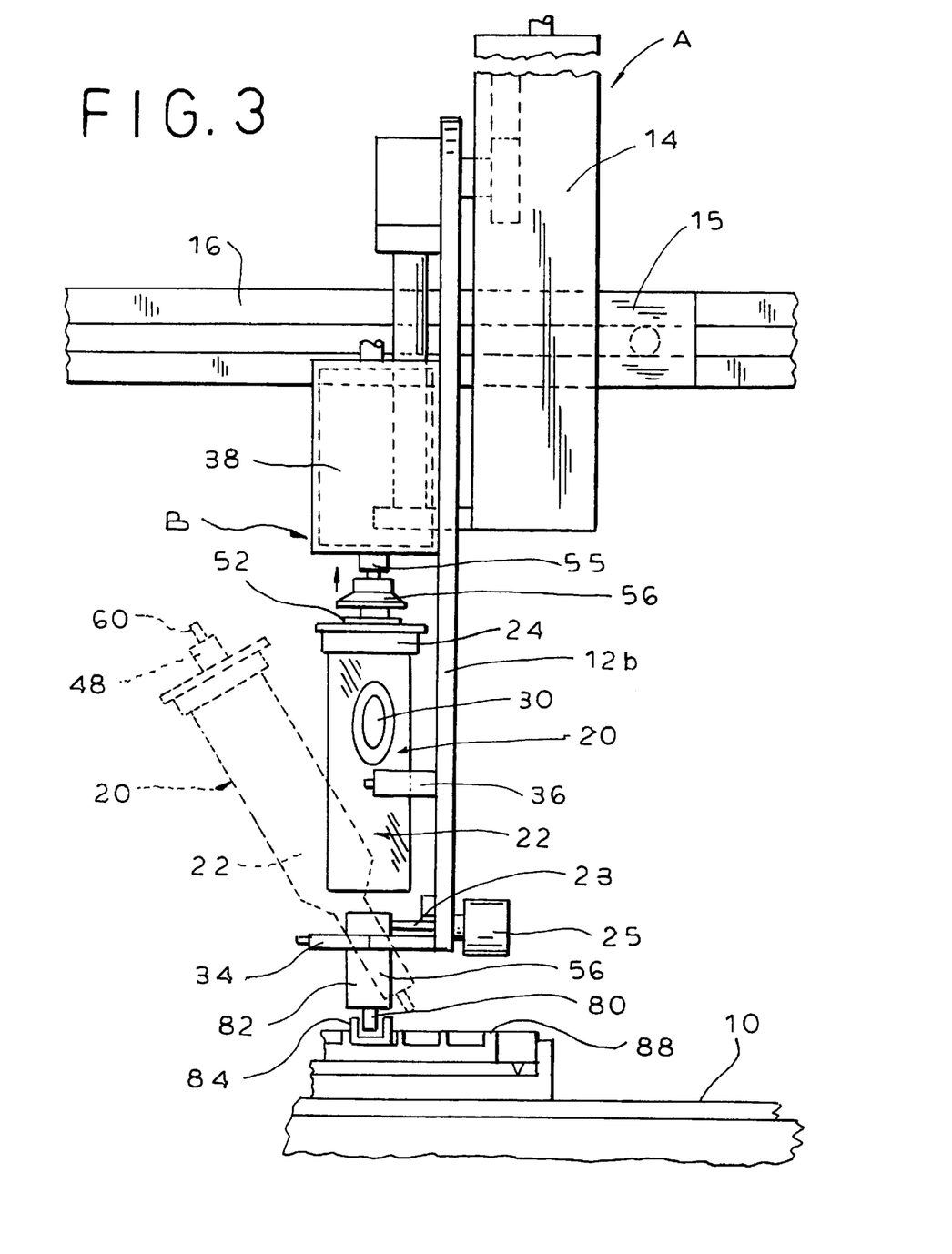
FIG. 3 is a side elevation view taken along line 3—3 of FIG. 2.

Main section 22 of reservoir 20 is retained on the branch by a holder 34 upon which the reservoir rests. Holder 34 extends horizontally from the bottom of the branch and has an opening into which the lower section 26 of the reservoir is received. As best seen in FIG. 3, a screw 23 with an enlarged head 25 is provided adjacent to holder 34 to secure the reservoir on the holder. The main section 22 of reservoir 20 is also held on bracket 12 by a clamp 36 which partially surrounds the body of the reservoir.

Figure 4A:
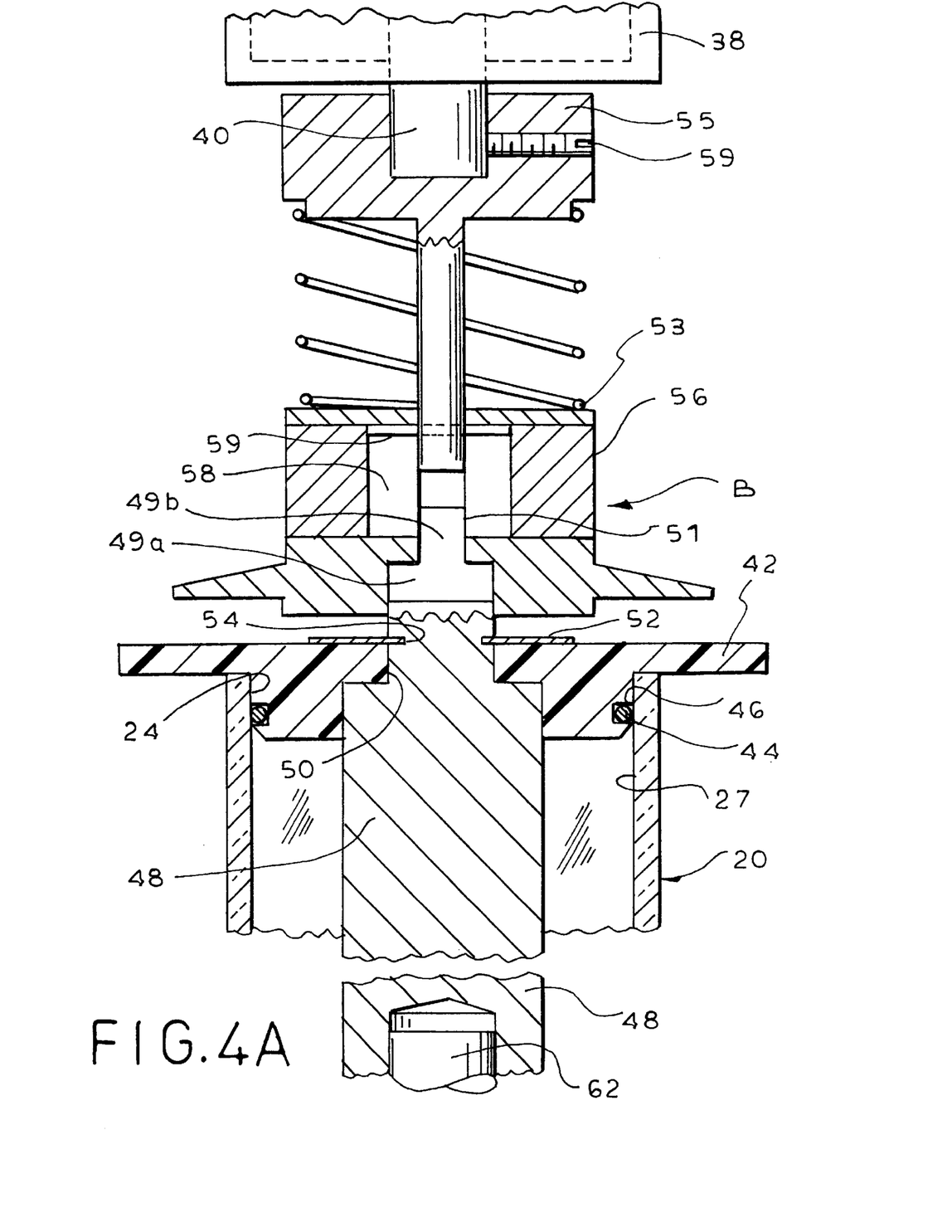
FIGS. 4A and 4B together are an enlarged side elevational view taken along line 4A—4A, 4B—4B of FIG. 2.

Mounted above each reservoir 20 is an electric drive motor 38 which rotates an output shaft 40. As best seen in FIG. 4A, reservoir 20 is provided with a removable cap 42 which covers mouth 24. Cap 42 is sealed to the interior wall 27 of the reservoir by an O-ring 44 which is seated in a circumferential groove 46 in the cap.

A shaft 48 extends vertically through an opening 50 in cap 42. Shaft 48 is held on cap 42 by a metal clip 52 which is received in a circumferential groove 54 in the shaft surface such that the shaft can rotate freely relative to cap 42. Removal of clip 52 permits shaft 48 to be removed from cap 42.

The top of shaft 48 ends in flat portion 49 with a wider section 49a and a narrower section 49b. Mounted over portion 49 of shaft 48 is a drive link ring 56 with a recess 51 shaped to correspond to the shape of shaft portion 49. Ring 56 is spring loaded toward the shaft by spring 53 situated between the top surface of ring 56 and the bottom surface of part 55. Part 55 is attached to shaft 40 and held by a set screw 57. The lower end of part 55 is fixed to ring 56 by a dowell pin 59. Ring 56 has a milled channel 58 in which pin 59 is received. Moving ring 56 away from cap 42 disengages the ring, and hence shaft 40 of motor 38 from shaft 48, allowing the reservoir to be pivoted from its vertical position, as seen in phantom in FIG. 3, and removed from the apparatus for cleaning or maintenance.

Figure 4B:
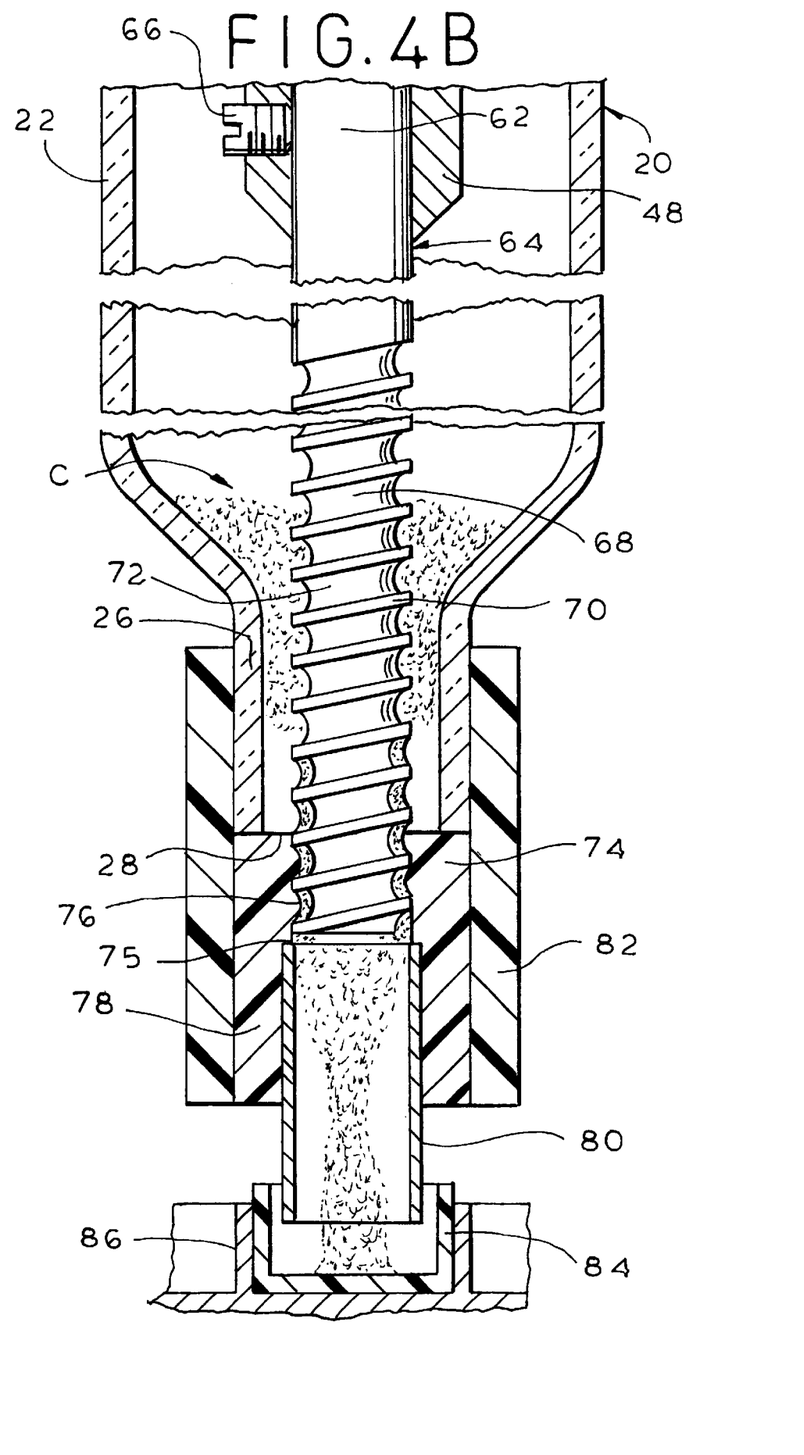
Figure 5:
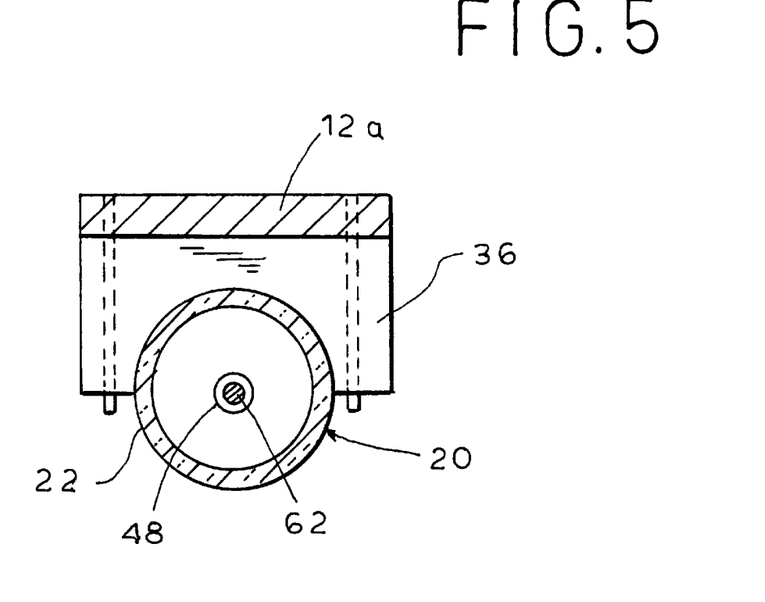
FIG. 5 is a top cross-sectional view taken along line 5—5 of FIG. 2.
Figure 6:
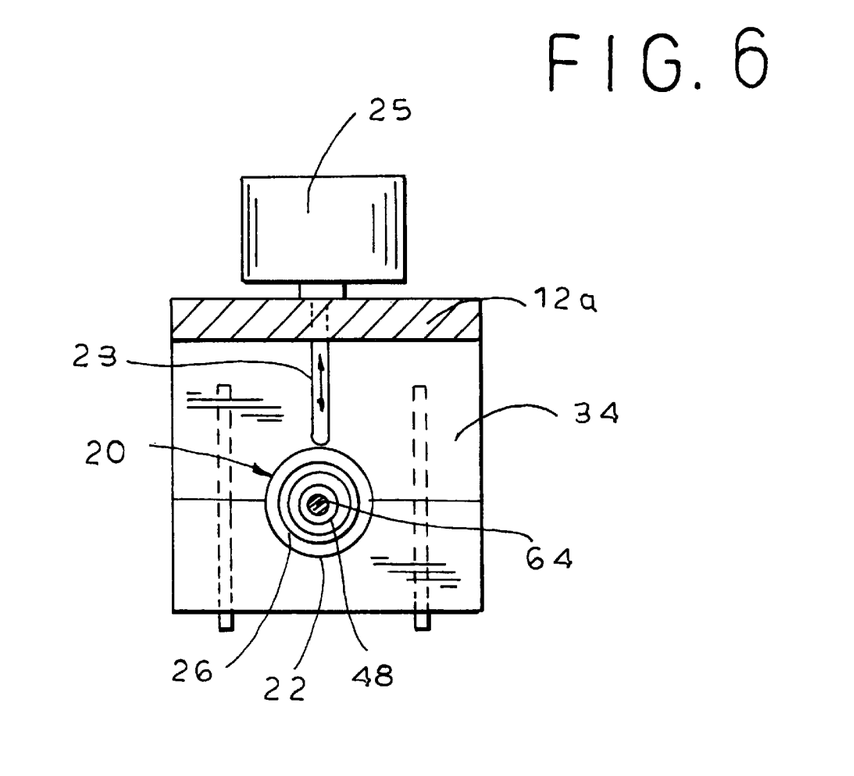
FIG. 6 is a top cross-sectional view taken along line 6—6 of FIG. 2.

The lower end of shaft 48 is hollow. The upper end 62 of a screw or auger 64 is received within shaft 48 and held in place by a set screw 66, see FIG. 4b. The lower exposed end 68 of screw 64 is externally threaded, forming a helical blade 70. Blade 70 extends radially outwardly of the central portion 72 of the screw. The bottom of screw 64 extends through the outlet 28 of reservoir 20 which has an inner diameter considerably larger than the outer diameter of the screw. The lower end of screw 64 is received in a silicone sleeve 74. Blade 70 is in direct contact with the interior surface 76 of sleeve 74 formed of a section of commercially available silicone C—Flex tubing. A silicone tube is used because of its compliant properties. Aside from maintaining direct contact with the blade, it retains the integrity of the resin, whereas a rigid tube would cause the screw to grind the resin between the blade and sleeve surface, destroying the resin particles. The relative sizes of the screw and sleeve are chosen such that the outer diameter of the edge of blade 70 is at least as large, and preferably slightly larger, than the inner diameter of sleeve 74. Thus, the interior surface 76 of sleeve 74 is deformed slightly by the blade.

The bottom portion 78 of sleeve 74 receives a thin wall stainless steel tube 80, preferably No. 8 gauge, through which the powder, generally designated C, passes after it is released from the helical groove defined between blade 70 and sleeve 74. The top of tube 80 is preferably spaced a short distance 75, preferably 1/16 in., from the end of screw 64. The bottom of tube 80 extends beyond the end of sleeve 74. The internal diameter of tube 80 is slightly larger than the external diameter of the screw blade.

An external elastic retaining sleeve 82 surrounds sleeve 74 and reduced diameter section 26 of reservoir 20, so as to retain sleeve 74 in a fixed position relative to reservoir 20. Sleeve 82 is also preferably a section of commercially available silicone C-Flex tubing. For example, sleeve 74 may have a 1/4 in. outer diameter, a 1/8 in. inner diameter and may be 3/8 in. long. Sleeve 82 may have a 1/4 in. inner diameter, a 3/8 in. outer diameter and be 3/4 in. long.

The apparatus can be configured to dispense 3 to 15 mg. of powder into each container. Filling the containers takes approximately 45–60 minutes.

Figure 7:
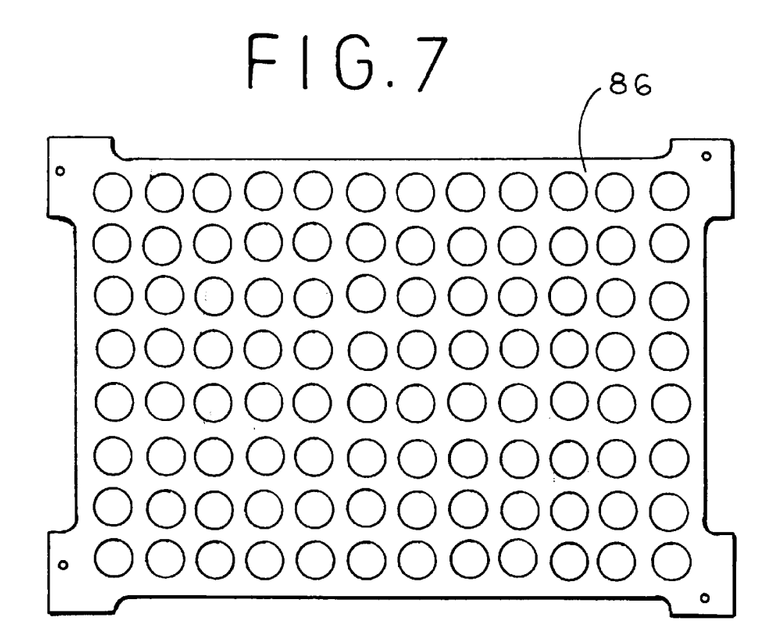
FIG. 7 is a top plan view of a container tray.
Figure 8:
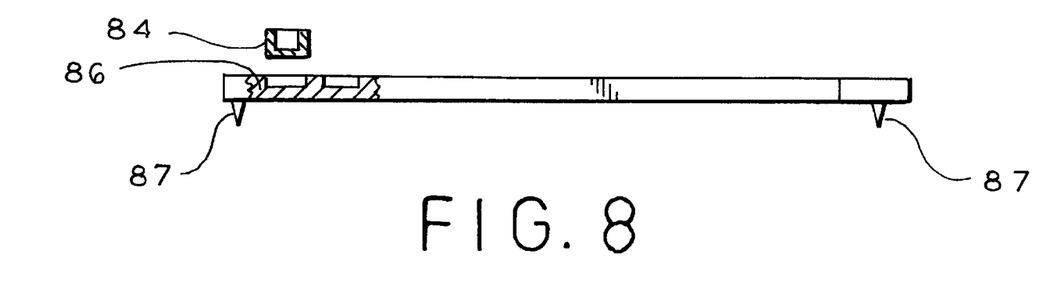
FIG. 8 is a side partially cut-away view of the tray of FIG. 7.

For pharmaceutical applications, the containers may take the form of NanoKans 84. Powder C is dispensed into the NanoKans which are preferably situated in an array. The NanoKans are typically situated in recesses in a tray 86, best seen in FIGS. 7 and 8. Tray 86 sits atop pointed feet 87.

Figure 9:
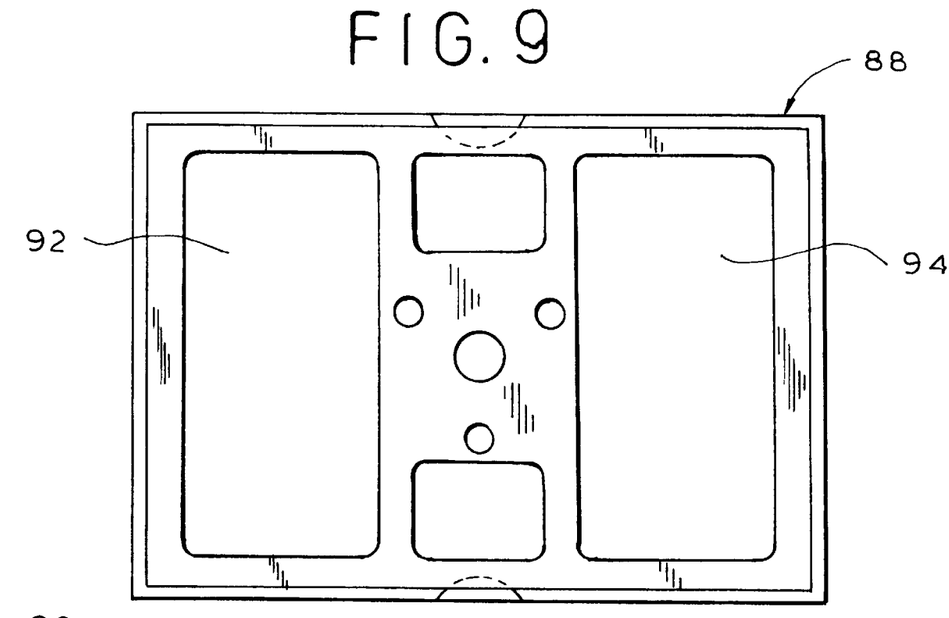
FIG. 9 is a top elevational view of the top of one of the scale platforms.
Figure 10:
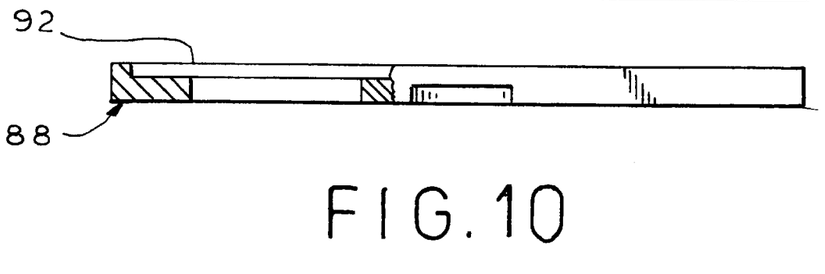
FIG. 10 is a side, partially cut away view of the platform of FIG. 9.

Referring back to FIG. 1, two trays 86a and 86b, holding arrays of NanoKans 84 are provided, one for each branch 12a, 12b of bracket 12. Each tray 86a, 86b is placed upon a scale platform 88a, 88b, one of which is illustrated in FIGS. 9 and 10. Each scale platform 88a, 88b is part of an electronic scale 90a, 90b. Each electronic scale generates an output signal which is a function of the weight upon its platform.

Each scale platform 88 has first and second openings 92, 94 to reduce its weight. A guide 96 is fixed to work surface 10 in a position parallel to track 16, between platforms 88.

A "T" square tray positioner part 98 is slideably mounted on guide 96. Part 98 has two extensions 98a, 98b which are collinear and perpendicular to guide 96 and hence to track 16. Trays 86a and 86b are situated adjacent portions 98a, 98b of part 98, respectively, such that movement of part 98 aligns trays 86 on platforms 88 and hence relative to bracket 12 such that mechanism A will properly align each of the powder dispenser assemblies B on bracket 12 with the NanoKans 84 in each tray 86, in sequence.

A computer (not shown) is employed to move the powder dispenser assemblies mounted to each branch of bracket 12 through positions in the X-Y plane into alignment with the NanoKans in each tray and once aligned, downwardly, along track 14, such that the tube 80 at the bottom of the dispenser is received in the interior of the aligned NanoKan. The computer also actuates each drive motor 38 to rotate the attached screw 64, through connecting shift 48, such that powder C is dispensed into the NanoKan.

The speed of drive motors is regulated by the computer such that each screw 64 rotates at a first, relatively high, rate during the initial portion of each dispensing operation and then at a second, relatively low, rate during the final portion of the dispensing operation. About 80% of the desired weight of powder is dispensed during the first period. Thus, the bulk of the powder is dispensed very rapidly. The output signal of each of the scales is monitored only during the final portion of the dispensing operation, that is, during the low rotational rate period. This is because it is only during that portion of the dispensing operation when it is necessary to monitor the weight of powder dispensed such that each drive motors can be deactuated at precisely the time when the required weight of powder has been dispensed into the NanoKan.

Deactuating the drive motor causes the rotation of the screw 64 within sleeve 74 to cease. Because of the contact between blade 70 and the inner surface of sleeve 74, powder flow stops completely upon deactuation of the drive motor, as no powder can pass between the blade and sleeve.

Bracket 12 is then moved upwardly, along the Z axis, to align the assemblies with the next NanoKans in sequence. Once aligned with the next NanoKans, bracket 12 is moved downwardly, along the Z axis, to insert sleeves 80 into the aligned NanoKans. The drive motors are then energized and the dispensing operation is repeated.

All of this takes place very rapidly. Because of the screw/sleeve configuration, the quantity of powder dispensed can be precisely controlled, under all conditions, even when the powder is rapidly dispensed.

While only a single preferred embodiment of the present invention has been disclosed for purposes of illustration, it is obvious that many variations and modifications could be made thereto. It is intended to cover all of these variations and modifications which fall within the scope of the present invention, as defined by the following claims:

We claim:

1. A powder dispensing assembly comprising a powder reservoir with an outlet, a compliant sleeve having an inner surface, said sleeve being situated proximate said reservoir outlet, a rotatable screw having a blade, said screw being at least partially received within said sleeve with said screw blade in contact with said inner surface of said sleeve, drive means for rotating said screw relative to said sleeve and a rigid tube, said rigid tube having one end received within said sleeve.

2. The assembly of claim 1 wherein the outer diameter of said blade is at least as large as the inner diameter of said sleeve.

3. A powder dispensing assembly comprising a powder reservoir having an outlet, a compliant sleeve having an inner surface, said sleeve being situated proximate said reservoir outlet, a rotatable screw having a blade, said screw being at least partially received within said sleeve, drive means for rotating said screw relative to said sleeve, said screw blade having an outer diameter which is at least as large as the inner diameter of said sleeve and a rigid tube, said rigid tube having an end received within said sleeve.

4. The assembly of claim 3 wherein said outer diameter of said screw blade is slightly larger than the inner diameter of the said sleeve.

5. The assembly of claim 1 or 3 wherein said sleeve comprises a section of silicone tube.

6. The assembly of claim 1 or 3 further comprising means for controlling said drive means to rotate said screw at a first rate during a first time period and at a second rate during a second time period.

7. The assembly of claim 1 or 3 wherein said one end of said rigid tube is spaced a short distance from said screw.

8. The assembly of claim 1 or 3 wherein said rigid tube has an outer diameter and wherein the outer diameter of said screw is approximately equal to the outer diameter of said rigid tube.

9. The assembly of claim 1 or 3 wherein said rigid tube has an outer diameter and said sleeve has an inner diameter and wherein said outer diameter of said rigid tube is approximately equal to said inner diameter of said sleeve.

10. The assembly of claim 1 or 3 adapted for dispensing powder into a plurality of containers in an array, further comprising means for moving said assembly into alignment with said containers in said array.

11. The assembly of claim 1 or 3 adapted for dispensing powder into a plurality of containers situated in first and second arrays, further comprising a second dispensing assembly and means for simultaneously moving said assemblies respectively into alignment with said containers in each of said arrays.

12. The assembly of claim 1 or 3 further comprising means for retaining said sleeve proximate said reservoir outlet.

13. The assembly of claim 12 wherein said reservoir outlet has an end and wherein said retaining means retains said sleeve adjacent said end of said reservoir outlet.

14. The assembly of claim 1 or 3 wherein said reservoir comprises a main section and an inlet section extending from said main section.

15. The assembly of claim 14 wherein said inlet section extends outwardly and upwardly from said main section.

16. The assembly of claim 1 or 3 further comprising means operably connecting said drive means and said screw.

17. The assembly of claim 16 further comprising means for mounting said drive means above said reservoir.

18. The assembly of claim 16 wherein said connecting means extends through said reservoir.

19. A powder dispensing assembly comprising a powder reservoir with an outlet, a compliant sleeve having an inner surface, said sleeve being situated proximate said reservoir outlet, a rotatable screw having a blade, said screw being at least partially received within said sleeve with said screw blade in contact with said inner surface of said sleeve, and drive means for rotating said screw relative to said sleeve and means for retaining said sleeve proximate said reservoir outlet, wherein said retaining means comprises a second compliant tube.

20. A powder dispensing assembly comprising a powder reservoir with an outlet, a compliant sleeve having an inner surface, said sleeve being situated proximate said reservoir outlet, a rotatable screw having a blade, said screw being at least partially received within said sleeve with said screw blade in contact with said inner surface of said sleeve, drive means for rotating said screw relative to said sleeve, further comprising means for controlling said drive means to rotate said screw at a first rate during a first time period and at a second rate during a second time period.

21. A powder dispensing assembly comprising a powder reservoir having an outlet, a compliant sleeve having an inner surface, said sleeve being situated proximate said reservoir outlet, a rotatable screw having a blade, said screw being at least partially received within said sleeve, and drive means for rotating said screw relative to said sleeve, said screw blade having an outer diameter which is at least as large as the inner diameter of said sleeve, further comprising means for controlling said drive means to rotate said screw at a first rate during a first time period and at a second rate during a second time period.

22. The assembly of claim 20 or 21 wherein said first rate is higher than said second rate.

23. The assembly of claim 20 or 21 adapted to dispense a predetermined weight of powder into a container, further comprising means for weighing said container and for generating signal which is a function of the weight of said container, said drive means control means being operably connected to receive said signal and to deactuate said drive means when said predetermined weight is reached.

24. The assembly of claim 23 wherein said weighing means is operational only during said second time period.

25. A powder dispensing assembly comprising a powder reservoir with an outlet, a compliant sleeve having an inner surface, said sleeve being situated proximate said reservoir outlet, a rotatable screw having a blade, said screw being at least partially received within said sleeve with said screw blade in contact with said inner surface of said sleeve, drive means for rotating said screw relative to said sleeve, said assembly being adapted for dispensing powder into a plurality of containers in an array, further comprising means for moving said assembly into alignment with said containers in said array.

26. A powder dispensing assembly comprising a powder reservoir having an outlet, a compliant sleeve having an inner surface, said sleeve being situated proximate said reservoir outlet, a rotatable screw having a blade, said screw being at least partially received within said sleeves and drive means for rotating said screw relative to said sleeve, said screw blade having an outer diameter which is at least as large as the inner diameter of said sleeve, said assembly being adapted for dispensing powder into a plurality of containers in an array, further comprising means for moving said assembly into alignment with said containers in said array.

27. The assembly of claim 25 or 26 wherein said assembly moving means comprises a bracket to which said assembly is mounted, means for moving said bracket to selected positions relative to said array, said positions being selected such that said assembly aligns with a different one of said containers in each of the positions.

28. The assembly of claim 27 wherein said bracket moving means moves said bracket to positions in the X-Y plane.

29. The assembly of claim 25 or 26 further comprising means for weighing said array, said weighing means comprising a platform upon which said array is situated and means for aligning said array with said bracket moving means.

30. The assembly of claim 29 wherein said array is situated in a tray and wherein said aligning means comprises a track fixed relative to said bracket moving means, a part having a surface adapted to abut said tray, said part being movable along said track.

31. The assembly of claim 30 wherein said track and said surface are fixed relative to each other.

32. A powder dispensing assembly comprising a powder reservoir with an outlet, a compliant sleeve having an inner surface, said sleeve being situated proximate said reservoir outlet, a rotatable screw having a blade, said screw being at least partially received within said sleeve with said screw blade in contact with said inner surface of said sleeve, drive means for rotating said screw relative to said sleeve, said assembly being adapted for dispensing powder into a plurality of containers situated in first and second arrays, further comprising a second dispensing assembly and means for simultaneously moving said assemblies respectively into alignment with said containers in each of said arrays.

33. A powder dispensing assembly comprising a powder reservoir having an outlet, a compliant sleeve having an inner surface, said sleeve being situated proximate said reservoir outlet, a rotatable screw having a blade, said screw being at least partially received within said sleeve, and drive means for rotating said screw relative to said sleeve, said screw blade having an outer diameter which is at least as large as the inner diameter of said sleeve, said assembly being adapted for dispensing powder into a plurality of containers situated in first and second arrays, further comprising a second dispensing assembly and means for simultaneously moving said assemblies respectively into alignment with said containers in each of said arrays.

34. The assembly of claim 32 or 33 wherein said assemblies moving means comprises a bracket to which each of said assemblies is mounted, means for moving said bracket to selected positions relative to said arrays, said positions being selected such that each assembly is aligned with one of said containers in a different one of said arrays in each of said positions.

35. The assembly of claim 34 wherein said bracket moving means moves said bracket to positions in the X-Y plane.

36. The assembly of claim 32 or 33 further comprising means for weighing each array, said weighing means comprising first and second platforms upon which said first and second arrays are respectively received.

37. The assembly of claim 36 further comprising means for aligning each of said arrays with said bracket moving means.

38. The assembly of claim 37 wherein the containers in each of said arrays are situated in a tray and wherein said aligning means comprises a track situated between said platforms, fixed relative to said bracket moving means, a part having first and second surfaces adapted to abut said first and second trays, respectively, said part being moveable along said track.

39. The assembly of claim 38 wherein said surfaces are collinear.

40. The assembly of claim 39 wherein said collinear surfaces are fixed relative to said track.

41. Automated apparatus for dispensing measured amounts of powder to containers in an array, said apparatus comprising a powder dispensing assembly, said powder dispensing assembly comprising a powder reservoir having an outlet, a compliant sleeve situated proximate said reservoir outlet, a screw at least partially rotatably received within said sleeve, said screw having a blade in contact with the inner surface of said sleeve, drive means for rotating said screw, means for moving said assembly relative to said array to selected positions in which said assembly aligns with the said containers in said array, means for weighing said array and for generating signals in accordance therewith, and means for controlling said screw drive means in accordance with said signals to dispense powder from said reservoir into said containers.

42. The apparatus of claim 41 wherein said means for controlling said drive means rotates said screw at a first rate during a first time period and at a second rate during a second time period for each dispensing operation and means for actuating said weighing means at the beginning of each second time period.

43. The apparatus of claim 42 wherein said first rate is higher than said second rate.

44. The apparatus of claim 41 further comprising means for aligning said array with said moving means.

45. The apparatus of claim 41 wherein the said containers in said array are situated in a tray and further comprising means for aligning said tray with said moving means.

46. The apparatus of claim 45 wherein said aligning means comprises a track mounted in fixed relation to said moving means, a part with a surface adapted to abut said tray, said part being movable along said track.

47. The apparatus of claim 46 wherein said surface is orthogonal with said track.

48. Automated apparatus for dispensing measured amounts of powder to containers in first and second arrays, said apparatus comprising a first and second powder dispensing assemblies, each of said assemblies comprising a powder reservoir with an outlet, a compliant sleeve situated proximate said reservoir outlet, a screw at least partially received within said sleeve, said screw having a blade in contact with the inner surface of said sleeve, drive means for rotating said screws, respectively, a bracket upon which each of said assemblies is mounted, means for moving said bracket relative to said arrays to selected positions in which each of said assemblies aligns with containers in one of said arrays, respectively, means for weighing each of said arrays and for generating signals in accordance therewith, and means for controlling said drive means to rotate said screws of said fist and second assemblies, respectively, in accordance with said signals.

49. The apparatus of claim 48 wherein said containers in each of said arrays are situated in first and second trays, respectively, and further comprising means for aligning said trays with said bracket moving means.

50. The apparatus of claim 49 wherein said aligning means comprises a track mounted in fixed relation to said bracket moving means, a part with a surface adapted to abut each of said trays, said part being movable along said track.

51. The apparatus of claim 50 wherein said surface is orthogonal with said track.

52. A powder dispensing assembly comprising a powder reservoir with an outlet, a compliant sleeve having an inner surface, said sleeve being situated proximate said reservoir outlet, a rotatable screw having a blade, said screw being at least partially received within said sleeve with said screw blade in contact with said inner surface of said sleeve, and drive means for rotating said screw relative to said sleeve, said reservoir outlet having an outer diameter, said sleeve having an outer diameter and wherein said outer diameter of said reservoir outlet is approximately equal to said outer diameter of said sleeve.

53. A powder dispensing assembly comprising a powder reservoir having an outlet, a compliant sleeve having an inner surface, said sleeve being situated proximate said reservoir outlet, a rotatable screw having a blade, said screw being at least partially received within said sleeves and drive means for rotating said screw relative to said sleeve, said screw blade having an outer diameter which is at least as large as the inner diameter of said sleeve, said reservoir outlet having an outer diameter, said sleeve having an outer diameter and wherein said outer diameter of said reservoir outlet is approximately equal to said outer diameter of said sleeve.

54. The assembly of claim 52 or 53 wherein said reservoir outlet has an inner diameter and said sleeve has an inner diameter and wherein said inner diameter of said reservoir outlet is larger than said inner diameter of said sleeve.

55. A powder dispensing assembly comprising a powder reservoir having an outlet, a compliant sleeve having an inner surface, said sleeve being situated proximate said reservoir outlet, a rotatable screw having a blade, said screw being at least partially received within said sleeve, and drive means for rotating said screw relative to said sleeve, said screw blade having an outer diameter which is at least as large as the inner diameter of said sleeve and means for retaining said sleeve proximate said reservoir outlet, said retaining means comprising a second compliant sleeve.

56. A powder dispensing assembly comprising a powder reservoir with an outlet, a compliant sleeve having an inner surface, said sleeve being situated proximate said reservoir outlet, a rotatable screw having a blade, said screw being at least partially received within said sleeve with said screw blade in contact with said inner surface of said sleeve, and drive means for rotating said screw relative to said sleeve and means for retaining said sleeve proximate said reservoir outlet, wherein said retaining means comprises a section of silicone tube.

57. A powder dispensing assembly comprising a powder reservoir having an outlet, a compliant sleeve having an inner surface, said sleeve being situated proximate said reservoir outlet, a rotatable screw having a blade, said screw being at least partially received within said sleeve, and drive means for rotating said screw relative to said sleeve, said screw blade having an outer diameter which is at least as large as the inner diameter of said sleeve and means for retaining said sleeve proximate said reservoir outlet, wherein said retaining means comprises a section of silicone tube.

58. A powder dispensing assembly comprising a powder reservoir with an outlet, a compliant sleeve having an inner surface, said sleeve being situated proximate said reservoir outlet, a rotatable screw having a blade, said screw being at least partially received within said sleeve with said screw blade in contact with said inner surface of said sleeve, and drive means for rotating said screw relative to said sleeve and means for retaining said sleeve proximate said reservoir outlet, wherein said retaining means at least partially surrounds said reservoir outlet and said sleeve.

59. A powder dispensing assembly comprising a powder reservoir having an outlet, a compliant sleeve having an inner surface, said sleeve being situated proximate said reservoir outlet, a rotatable screw having a blade, said screw being at least partially received within said sleeve, and drive means for rotating said screw relative to said sleeve, said screw blade having an outer diameter which is at least as large as the inner diameter of said sleeve and means for retaining said sleeve proximate said reservoir outlet, wherein said retaining means at least partially surrounds said reservoir outlet and said sleeve.

60. A powder dispensing assembly comprising a powder reservoir with an outlet, a compliant sleeve having an inner surface, said sleeve being situated proximate said reservoir outlet, a rotatable screw having a blade, said screw being at least partially received within said sleeve with said screw blade in contact with said inner surface of said sleeve, drive means for rotating said screw relative to said sleeve and means operably connecting said drive means and said screw, wherein said connecting means comprises a first part operably connected to said drive means and a second part operably connected to said screw, said second part having a given shape, said first part having a recess with a shape corresponding to said given shape and means for urging said first part towards said second part.

61. A powder dispensing assembly comprising a powder reservoir having an outlet, a compliant sleeve having an inner surface, said sleeve being situated proximate said reservoir outlet, a rotatable screw having a blade, said screw being at least partially received within said sleeve, and drive means for rotating said screw relative to said sleeve, and means operably connecting said drive means and said screw, wherein said connecting means comprises a first part wherein said connecting means comprises a first part operably connected to said drive means and a second part operably connected to said screw, said second part having a given shape, said first part having a recess with a shape corresponding to said given shape and means for urging said first part towards said second part.

* * * * *